United States Patent [19]

Harelstad et al.

[11] Patent Number: 4,714,838

[45] Date of Patent: Dec. 22, 1987

[54] SECOND HARMONIC GENERATION WITH N,N′-SUBSTITUTED BARBITURIC ACIDS

[75] Inventors: Roberta E. Harelstad, Eagan; John Stevens, Stillwater, both of Minn.

[73] Assignee: Minnesota Mining and Manufacturing Company, St. Paul, Minn.

[21] Appl. No.: 925,300

[22] Filed: Oct. 31, 1986

[51] Int. Cl.⁴ .............................................. H03F 7/00
[52] U.S. Cl. ................................. 307/427; 252/582; 252/583
[58] Field of Search .............................. 307/425, 427; 372/21–22; 252/582, 600

[56] References Cited

U.S. PATENT DOCUMENTS

| | | | |
|---|---|---|---|
| 3,395,329 | 7/1968 | Rentzepis | 321/69 |
| 3,431,484 | 3/1969 | Pao et al. | 321/69 |
| 3,858,124 | 12/1974 | Bass et al. | 332/7.51 |
| 4,199,698 | 4/1980 | Bethea et al. | 307/425 |
| 4,208,501 | 6/1980 | Yee et al. | 526/259 |
| 4,376,899 | 3/1983 | Chemla et al. | 307/425 |
| 4,395,473 | 7/1983 | Horie et al. | 430/58 |
| 4,431,263 | 2/1984 | Garito | 350/96.34 |
| 4,450,219 | 5/1984 | Horie et al. | 430/59 |
| 4,579,915 | 4/1986 | Choe | 525/435 |

FOREIGN PATENT DOCUMENTS 5235587  3/1977  United Kingdom ............... 307/427

Primary Examiner—James W. Davie
Assistant Examiner—Bertha Randolph
Attorney, Agent, or Firm—Donald M. Sell; James A. Smith; David L. Weinstein

[57] ABSTRACT

Devices for and method of generating coherent second harmonic light radiation. The devices comprise a laser source of coherent light radiation at a fixed fundamental frequency, a crystalline N,N′-substituted barbituric acid that crystallizes in a non-centrosymmetric configuration, means for directing the output radiation of the laser onto the N,N′-substituted barbituric acid, and output means for utilizing the second harmonic frequency.

12 Claims, 1 Drawing Figure

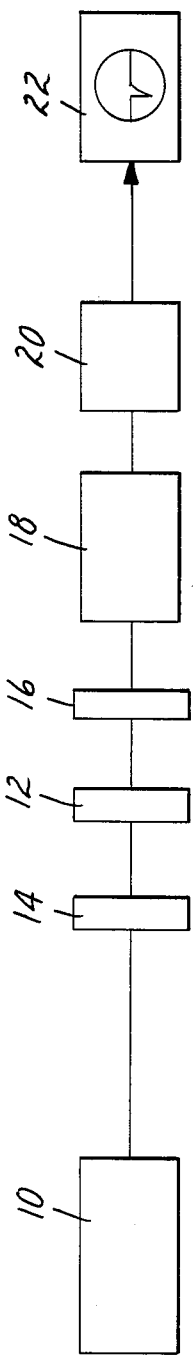

SECOND HARMONIC GENERATION WITH N,N'-SUBSTITUTED BARBITURIC ACIDS

TECHNICAL FIELD

This invention is concerned with materials for nonlinear optical devices for the conversion of optical energy at one frequency to optical energy at another frequency.

BACKGROUND OF THE INVENTION

Laser techniques have been developed so that it is possible to obtain a limited number of fundamental frequencies of coherent laser light by utilizing solid, gas, and liquid media. However, in many applications, laser light having frequencies not among the fundamental frequencies obtainable is required, and in some cases laser light exhibiting a continuous spectrum over a certain range of frequencies is required. Nonlinear optical crystals have, therefore, frequently been employed to convert coherent laser light of a fundamental frequency into laser light of the second harmonic, that is to say, laser light with a frequency twice the fundamental frequency.

In the prior art, monocrystalline forms of potassium dihydrogen phosphate (KDP), ammonium dihydrogen phosphate (ADP), barium sodium niobate (BaNaNbO$_3$), and lithium niobate (LiNbO$_3$) have been used for generating higher frequency harmonics. Monocrystalline KDP and ADP, while offering greater resistance to optical irradiation induced surface damage due to laser beam bombardment, do not exhibit large optical nonlinearities. This rendered these crystals unfavorable for higher harmonic frequency generation or conversion. In contrast, BaNaNbO$_3$ and LiNbO$_3$ show large nonlinearities but, unfortunately, a low resistance to optical damage. In this regard, the term "resistance to optical damage" means the number of times the surface of a crystalline material can be bombarded (shots) with laser radiation of a given power density in watts per unit area before the subject crystal shows signs of opacity. Thus, a crystal showing high resistance can sustain a larger number of shots than a crystal of low resistance for the same power density of the incident laser beams.

The possibility of using organic molecules in nonlinear optical devices has generated much interest recently because a large number of molecules are available for investigation. Some substituted aromatic molecules are known to exhibit large optical nonlinearities. The possibility of such an aromatic molecule having large optical nonlinearities is enhanced if the molecule has donor and acceptor groups bonded at opposite ends of the conjugated system of the molecule. The potential utility for very high frequency application of organic materials having large second-order and third-order nonlinearities is greater than that for conventional inorganic electro-optic materials because of the bandwidth limitations of inorganic materials. Furthermore, the properties of organic materials can be varied to optimize mechanical and thermo-oxidative stability and laser damage threshold.

U.S. Pat. No. 4,199,698 discloses that the nonlinear optical properties of 2-methyl-4-nitroaniline (MNA) make it a highly useful material in nonlinear devices that convert coherent optical radiation including a first frequency into coherent optical radiation including a second frequency. The nonlinear devices have means for introducing coherent radiation of a first frequency into the MNA and means for utilizing coherent radiation emitted from the MNA at a second frequency.

U.S. Pat. No. 4,431,263 discloses that diacetylenes and polymers formed from diacetylenic species, which are amendable to close geometric, steric, structural, and electronic control, provide nonlinear optic, waveguide, piezoelectric, and pyroelectric materials and devices. Diacetylenes which are crystallizable into crystals having a noncentrosymmetric unit cell may form single crystals or be elaborated into a thin film upon a substrate by the Langmuir-Blodgett technique. Such films may be polymerized either thermally or by irradiation for use in nonlinear optical systems. Diacetylenes are covalently bonded to substrates through the employment of silane species and subsequently polymerized to yield nonlinear optic devices having high structural integrity in addition to high efficiencies and optical effects.

Other U.S. patents relating to non-linear optical properties of organic materials include U.S. Pat. Nos. 4,208,501; 4,376,899; and 4,579,915.

SUMMARY OF THE INVENTION

The present invention provides a laser generator of coherent second harmonic light radiation by utilizing certain N,N'-substituted barbituric acids and a method of generating coherent second harmonic light radiation with such a device.

In general, second harmonic generators of this invention comprise, in combination, a laser source of coherent light radiation at a fixed fundamental frequency, an organic molecular crystalline compound selected from particular classes of N,N'-substituted barbituric acids, means for directing the output radiation of the laser onto the organic molecular crystalline N,N'-substituted barbituric acid, and output means for utilizing the second harmonic frequency.

BRIEF DESCRIPTION OF THE DRAWINGS

The drawing is a diagrammatic representation of a suitable arrangement for demonstrating the second harmonic generating properties of the N,N'-substituted barbituric acids of this invention.

DETAILED DESCRIPTION

Barbituric acids are characterized as a six-membered 1,3-diazine ring having three carbonyl groups in the 2-, 4-, and 6- positions of the six-membered ring. The barbituric acids that are useful in the present invention are substituted at both the 1- and 3- positions, and, optionally at the 5-position. Barbituric acids that have been found to exhibit second harmonic generation are crystalline in form, and are preferably in solid crystalline form. While barbituric acids in liquid crystalline form may also exhibit second harmonic generation, detection of signals from barbituric acids in liquid crystalline form is difficult. Regardless of whether they are in solid crystalline form or in liquid crystalline form, barbituric acids suitable for this invention must have a non-centrosymmetric configuration. Non-centrosymmetric species are those which have no center of symmetry on either the molecular or crystalline unit cell level.

N,N'-substituted barbituric acids that have been found to be preferable for this invention can be represented by the following general formula:

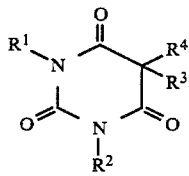

where

R[1] and R[2] independently represent an alkyl group, an alkaryl group, an aralkyl group, or a heteroaromatic group, and R[3] and R[4] independently represent an alkyl group, an alkaryl group, an aralkyl group, a heteroaromatic group, an aromatic group, hydrogen, or R[3] and R[4] together, along with the carbon atom in the 5-position, form a ring, e.g. an aliphatic ring, containing from 3 to 7 ring members.

If R[1], R[2], R[3], or R[4] is an alkyl group, it preferably contains 1 to 18 carbon atoms, more preferably 1 to 6 carbon atoms. The alkyl group can be straight chain, branched, or, if there are a sufficient number of carbon atoms, cyclic. The alkyl group may be substituted or unsubstituted. If the group is substituted, it is preferred that at least one of the substituents have a sigma constant of from about 0.062 to about 0.778. As used herein, the term "sigma constant" means the Hammett substituent constant, $\sigma$para, based on the ionization of benzoic acid. This is the sigma constant of the para position. A compilation of sigma constants can be found in J. E. Leffler and E. Gruenwald, *Rates and Equilibria of Organic Reactions*, John Wiley and Sons (New York: 1963), p. 173. Representative examples of such substituents are —F ($\sigma=0.062$), —SCN ($\sigma=0.52$), —CN ($\sigma=0.66$), and —NO$_2$ ($\sigma=0.778$).

If R[1], R[2], R[3], or R[4] is an alkaryl or aralkyl group, it preferably contains 1 to 18 carbon atoms, more preferably 1 to 4 carbon atoms in the alkyl moiety and 6 to 10 ring carbon atoms in the aryl moiety. The aryl moiety can comprise one ring or two fused rings. The alkyl moiety can be a straight chain, branched, or, if there are a sufficent number of carbon atoms, cyclic. The alkaryl or aralkyl group can be substituted or unsubstituted, and, if they are substituted, it is preferred that at least one of the substituents have a sigma constant of from about 0.062 to about 0.778.

If R[1], R[2], R[3], or R[4] is a heteroaromatic group, it can consist of one ring or two fused rings, where the hetero atom or atoms is selected from the group of atoms consisting of nitrogen, oxygen, and sulfur. The heteroaromatic group can be substituted or unsubstituted. If substituted, it is preferred that at least one of the substituents have a sigma constant of from about 0.062 to about 0.778.

If R[3], R[4], and the carbon atom in the 5-position form a ring, one of the ring members can be selected from the group of atoms consisting of oxygen, nitrogen, and sulfur. The carbon atom in the 5-position must be a tetrahedral carbon atom.

The aforementioned compounds are substantially transparent to electromagnetic radiation having wavelengths from 400–500 nm to 1000–1100 nm. Accordingly, the compounds are useful in second harmonic generators wherein both incident radiation and emergent radiation range from 400 nm to 1064 nm.

Barbituric acids can be readily synthesized by at least three methods. In the first method, a barbituric acid can be prepared by the condensation of a substituted urea and malonic acid using acetic anhydride as a condensing agent. In the second method, a barbituric acid can be prepared by the condensation of a substituted urea and malonic acid with the aid of a sodium alkoxide. In the third method, a barbituric acid can be prepared by the alkylation of 1,3-dimethylbarbituric acid with an alkylating agent, e.g., benzyl chloride.

Devices that are capable of generating coherent second harmonic light radiation with the N,N'-substituted barbituric acids described herein are well known in the art. Representative examples of such devices are described in U.S. Pat. Nos. 3,395,329, 3,431,484, and 3,858,124, all of which are incorporated herein by reference for the purpose of describing devices which can incorporate the N,N'-substituted barbituric acids described herein and exhibit efficient second harmonic generation by means of such incorporation.

Crystals were evaluated for SHG efficiency using the second harmonic generation (SHG) powder test described in Kurtz et al., J. Appl. Phys. 39, 3798, 1968. Each sample was ground and sieved and then mixed with a fluid, i.e., a liquid, to minimize refraction caused by differences in the index of refraction between the particles and the ambient atmosphere. The index-matched sample was placed between cell flats spaced 0.35±0.02 mm apart. Particles having mean diameters greater than 90 micrometers but less than 180 micrometers were used. Each sample was mixed with a drop of index matching fluid (Cargille n=1.63 or n=1.58 fluids or n=1.631 Convalex oil). The samples were not indexed matched critically, so that the actual SHG efficiencies may be higher than that reported in the examples.

Referring now to FIG. 1, infrared radiation at 1064 nm from a Q-switched Nd-YAG laser 10 was weakly focused onto the cell 12 containing the prepared sample. In the device illustrated in FIG. 1, the means for directing the output radiation of the laser, e.g. a lens, first through a filter 14 (Corning CS2-60 color filter used to block any radiation at 532 nm) and then onto the cell 12 containing the barbituric acid sample was integrated into the laser 10 and is not shown as a separate component. Means for directing the output radiation of the laser onto the organic molecular crystalline compound are well-known to one of ordinary skill in the art. An infrared blocking filter 16 placed behind the sample allowed only the second harmonic frequency radiation to pass through a ¼ meter monochrometer 18 tuned at 532 nm. The output of the monochrometer 18 was directed to a photomultiplier tube 20, and the resulting signal was processed by a boxcar averager 22 that averages over many laser pulses. Urea was the chosen standard because of its high second order coefficient and its ready availability. The urea standard was prepared in the same manner as the samples. The urea standard was indexed matched reasonably well, with a mismatch of about 0.01. The reported efficiency of a sample is its SHG signal normalized to that of the urea standard measured under the same experimental conditions.

The following examples are meant to illustrate, but not limit this invention. Parts and percentages are by weight unless otherwise indicated. All of the compounds prepared in the examples and comparative examples were characterized by standard analytical techniques, e.g. infrared spectroscopy, ultraviolet/visible absorption spectroscopy, nuclear magnetic resonance spectroscopy, melting point, and elemental analysis.

Second harmonic generation measurements are shown in Table I, which follows the examples.

EXAMPLE 1

Preparation of
1,3-Dimethyl-2,4,6-(1H,3H,5H)-Pyrimidinetrione

Acetic anhydride (80 ml, 0.84 mole) was added dropwise over three hours to a solution of 1,3-dimethylurea (32 g, 0.36 mole) and malonic acid (36 g, 0.35 mole) in acetic acid (80 ml) at 65° C. After the addition was complete, the temperature was raised and held at 90° C. for four hours. At the end of this period, the solvent was evaporated under reduced pressure and the residue boiled with ethanol for fifteen minutes. 1,3-Dimethyl-2,4,6-(1H,3H,5H)- pyrimidinetrione, collected by filtration, was recrystallized from ethanol as white needles (32.7 g, 58% yield), m.p. 122°–123° C.

EXAMPLE 2

Preparation of
1,3-Diethyl-2,4,6-(1H,3H,5H)-Pyrimidinetrione

Acetic anhydride (16 ml, 0.15 mole) was added dropwise over two hours to a solution of 1,3-diethylurea (5.3 g, 0.05 mole) and malonic acid (5.2 g, 0.05 mole) in acetic acid (40 ml) at 65° C. After the addition was complete, the temperature was raised to 90° C. and maintained there for three hours. The solvent was evaporated under reduced pressure and the residue boiled with ethanol for fifteen minutes. After some time, 1,3-diethyl-2,4,6-(1H,3H,5H)- pyrimidinetrione crystallized in cubic crystals, m.p. 52° C.

EXAMPLE 3

Preparation of
1,3-Dipropyl-2,4,6-(1H,3H,5H)-Pyrimidinetrione 1,3-Dipropylurea was prepared by the reaction of propylamine (8.2 ml, 0.1 mole) and propylisocyanate (9.4 ml, 0.1 mole) in ether (100 ml) at 4° C. Propylisocyanate was added dropwise over three hours with stirring to propylamine and the resultant dipropylurea precipitate was isolated by filtration. The product was obtained as colorless crystals (12 g, 86% yield), m.p. 104° C.

Acetic anhydride (16.5 ml, 0.05 mole) was added dropwise over three hours to a solution of 1,3-dipropylurea (7.5 g, 0.05 mole) and malonic acid (5.2 g, 0.05 mole) in acetic acid (40 ml) at 65° C. After the addition was completed, the temperature was raised to 90° C. and maintained for three hours. The solvent was evaporated under reduced pressure and the residue, 1,3-dipropyl-2,4,6-(1H,3H,5H)- pyrimidinetrione, solidified upon cooling. It was recrystallized from cyclohexane to provide colorless needles (7 g, 0.03 mole, 66% yield), m.p. 120°–121° C.

EXAMPLE 4

Preparation of
1,3-Diisopropyl-2,4,6-(1H,3H,5H)-Pyrimidinetrione

Isopropylisocyanate (9.8 ml, 0.1 mole) was added dropwise over three hours to a solution of isopropylamine (8.5 ml, 0.1 mole) in ether (100 ml) at 4° C., with stirring, and the product precipitated. Colorless crystals of the diisopropyl urea were obtained (12 g, 86% yield), m.p. 192°.

1,3-Diisopropyl-2,4,6-(1H,3H,5H)-pyrimidinetrione was prepared by the dropwise addition of acetic anhydride (40 ml) over three hours to a solution of 1,3-diisopropylurea (7.5 g, 0.05 mole) and malonic acid (5.2 g, 0.05 mole) at 65° C. After the addition was completed, the temperature was raised to 90° C. and maintained for three hours. The solvent was evaporated under reduced pressure and the residue solidified upon cooling. 1,3-Diisopropyl-2,4,6-(1H,3H,5H)-pyrimidinetrione recrystallized from cyclohexane as colorless needles (7.3 g, 70% yield), m.p. 79°–82°.

EXAMPLE 5

Preparation of
1,3-Di-(4-Nitrophenyl)-2,4,6-(1H,3H,5H)-Pyrimidinetrione 1,3-Di-(4-nitrophenyl)urea was prepared by the dropwise addition of a solution of p-nitrophenylisocyanate (16.4 g, 0.1 mole) in dimethyl formamide (150 ml) to a solution of p-nitroaniline (13.8 g, 0.1 mole) in dimethylformamide (130 ml) at 4° C. 1,3-Di-(4-nitrophenyl)urea precipitated slowly as a yellow solid.

1,3-Di-(4-nitrophenyl)urea (1.8 g, 0.006 mole), diethyl malonate (1 ml, 0.006 mole), and sodium hydroxide (0.24 g, 0.006 mole) were refluxed in ethanol (100 ml) for three hours. 1,3-Di-(4-nitrophenyl)-2,4,6-(1H,3H,5H)-pyrimidinetrione precipitated as a yellow powder, m.p. greater than 250° C.

EXAMPLE 6

Preparation of
1-Methyl-3-Phenyl-2,4,6-(1H,3H,5H)-Pyrimidinetrione

1-Methyl-3-phenylurea was prepared by the dropwise addition of methylisocyanate (6 ml, 0.1 mole) over three hours to an ether solution (100 ml) containing aniline (9 ml, 0.1 mole) at 4° C. with stirring. 1-Methyl-3-phenylurea precipitated as purple crystals which were recrystallized from ethanol, m.p. 150° C.

Acetic anhydride (16 ml, 0.17 mole) was added dropwise over three hours to a solution of 1-methyl-3-phenylurea (6 g, 0.04 mole) and malonic acid (4.6 g, 0.04 mole) in acetic acid (40 ml) at 60° C. After the addition was completed, the temperature was raised to 90° C. and maintained for four hours. The solvent was evaporated and the resulting residue treated with 0.1N NaOH (50 ml). After filtration, the solution was acidified with 0.2N HCl (120 ml). The solution was evaporated to dryness under reduced pressure, leaving solid 1-methyl-3-phenyl-2,4,6-(1H,3H,5H)- pyrimidinetrione upon cooling. It was recrystallized from ethanol to yield colorless crystals, m.p. 122.5°–123° C.

EXAMPLE 7

Preparation of
1,3,5-Trimethyl-2,4,6-(1H,3H,5H)-Pyrimidinetrione

A mixture of 1,3-dimethylurea (4.4 g, 0.05 mole) and diethyl methylmalonate (8.7 g, 0.05 mole) was boiled under reflux for twelve hours with three (3) equivalents of sodium in isopropanol. The solvent was evaporated under vacuum, and the resulting residue was dissolved in water and extracted with ether to remove salts. The product was precipitated with concentrated hydrochloric acid and collected by filtration. 1,3,5-Trimethyl-2,4,6-(1H,3H,5H)-pyrimidinetrione was recrystallized from cyclohexane as colorless needles (3.2 g, 40% yield), m.p. 87°–88° C.

EXAMPLE 8

Preparation of 1,3-Dimethyl-5,5-Dibenzyl-2,4,6-(1H,3H,5H)-Pyrimidinetrione 1,3-Dimethylbarbituric acid (5 g, 0.03 mole) was dissolved in 5% sodium hydroxide (30 ml) and diluted with ethanol (30 ml). Benzyl chloride (4.9 g, 0.38 mole) was then added. After slight heating and stirring for several minutes, the solution became acidic. The solution was made alkaline by the addition of sodium hydroxide, and 1,3-dimethyl-5,5-dibenzyl-2,4,6-(1H,3H,5H)-pyrimidinetrione precipitated. It was collected by filtration and recrystallized from ethanol to give white plates (4.1 g, 40% yield), m.p. 128°–129° C.

Table I below shows the second harmonic generation (SHG) efficiency relative to urea of the compounds prepared in Examples 1–8.

TABLE I

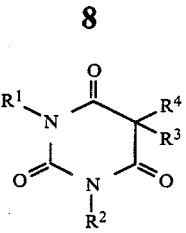

| Example | $R^1$ | $R^2$ | $R^3$ | $R^4$ | SHG efficiency |
|---|---|---|---|---|---|
| 1 | —$CH_3$ | —$CH_3$ | —H | —H | 3 |
| 2 | —$C_2H_5$ | —$C_2H_5$ | —H | —H | 3 |
| 3 | n-$C_3H_7$ | n-$C_3H_7$ | —H | —H | <0.001 |
| 4 | i-$C_3H_7$ | i-$C_3H_7$ | —H | —H | 0.004 |
| 5 | —$C_6H_4NO_2$ | —$C_6H_4NO_2$ | —H | —H | 1.3 |
| 6 | —$CH_3$ | —$C_6H_5$ | —H | —H | <0.001 |
| 7 | —$CH_3$ | —$CH_3$ | —$CH_3$ | —H | <0.001 |
| 8 | —$CH_3$ | —$CH_3$ | —$C_7H_7$ | —$C_7H_7$ | 0.002 |

From the foregoing table, it can be seen that when $R^1$ and $R^2$ are both methyl or both ethyl, the SHG efficiency is three times that of urea. When $R^1$ and $R^2$ are both —$C_6H_4NO_2$, the SHG efficiency is 1.3 times that of urea.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A second harmonic generator comprising a laser source of coherent light radiation at a fixed fundamental frequency, an organic molecular crystalline compound, means for directing the output radiation of the laser onto the compound, and output means for utilizing the second harmonic frequency, said compound being a N,N'-substituted barbituric acid which crystallizes in a non-centrosymmetric configuration, said compound being transparent to radiation at said fixed fundamental frequency and said second harmonic frequency.

2. The second harmonic generator of claim 1 wherein said organic molecular crystalline compound is represented by the formula:

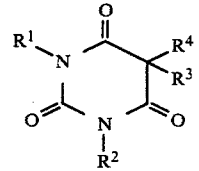

where
$R^1$ and $R^2$ independently represent an alkyl group, an alkaryl group, an aralkyl group, or a heteroaromatic group, and
$R^3$ and $R^4$ independently represent an alkyl group, an alkaryl group, an aralkyl group, a heteroaromatic group, an aromatic group, hydrogen, or $R^3$ and $R^4$ together, along with the carbon atom in the 5-position, form a ring containing from 3 to 7 ring members.

3. The second harmonic generator of claim 2 wherein $R^1$ represents an alkyl group having from 1 to 18 carbon atoms.

4. The second harmonic generator of claim 2 wherein $R^2$ represents an alkyl group having from 1 to 18 carbon atoms.

5. The second harmonic generator of claim 2 wherein $R^1$ represents a methyl group or an ethyl group and $R^2$ represents a methyl group or an ethyl group.

6. The second harmonic generator of claim 2 wherein at least one of $R^1$, $R^2$, $R^3$, or $R^4$ is alkyl group having at least one substituent thereon, wherein said at least one substituent has a sigma constant of from about 0.062 to about 0.778.

7. The second harmonic generator of claim 2 wherein the ring formed by $R^3$, $R^4$, and the carbon atom in the 5-position contains one ring member selected from the group of atoms consisting of oxygen, nitrogen, and sulfur.

8. The second harmonic generator of claim 1 wherein the laser is a Nd-YAG laser.

9. The second harmonic generator of claim 1 wherein said compound is a solid.

10. A process for converting a fixed fundamental frequency of coherent laser light into a second harmonic frequency which comprises passing said laser light through a nonlinear optical element comprising an organic molecular crystalline compound, said compound being a N,N'-substituted barbituric acid which crystallizes in a non-centrosymmetric configuration, said compound being transparent to said fixed fundamental frequency and to said second harmonic frequency.

11. The process of claim 9 wherein said organic molecular crystalline compound is represented by the formula:

where
$R^1$ and $R^2$ independently represent an alkyl group, an alkaryl group, an aralkyl group, or a heteroaromatic group, and
$R^3$ and $R^4$ independently represent an alkyl group, an alkaryl group, an aralkyl group, a heteroaromatic group, an aromatic group, hydrogen, or $R^3$ and $R^4$ together, along with the carbon atom in the 5-position, form a ring containing from 3 to 7 ring members.

12. The process of claim 11 wherein at least one of $R^1$, $R^2$, $R^3$, or $R^4$ is alkyl group having at least one substituent thereon, wherein said at least one substituent has a sigma constant of from about 0.062 to about 0.778.

* * * * *